United States Patent
Wyler et al.

(10) Patent No.: US 7,917,225 B2
(45) Date of Patent: Mar. 29, 2011

(54) SYSTEMS AND METHODS FOR SELECTING STIMULATION SITES AND APPLYING TREATMENT, INCLUDING TREATMENT OF SYMPTOMS OF PARKINSON'S DISEASE, OTHER MOVEMENT DISORDERS, AND/OR DRUG SIDE EFFECTS

(75) Inventors: Allen Wyler, Seattle, WA (US); Brad Fowler, Woodinville, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 668 days.

(21) Appl. No.: 11/489,074

(22) Filed: Jul. 18, 2006

(65) Prior Publication Data

US 2006/0253170 A1 Nov. 9, 2006

Related U.S. Application Data

(62) Division of application No. 10/986,614, filed on Nov. 12, 2004, now Pat. No. 7,565,200.

(51) Int. Cl.
*A61N 1/18* (2006.01)
(52) U.S. Cl. ............... 607/58; 607/45; 607/46; 607/63
(58) Field of Classification Search .............. 607/45, 607/46, 117, 120, 58
See application file for complete search history.

(56) References Cited

U.S. PATENT DOCUMENTS

| | | |
|---|---|---|
| 2,716,226 A | 8/1955 | Jonas |
| 2,721,316 A | 10/1955 | Shaw |
| 3,628,193 A | 12/1971 | Collins |
| 3,650,276 A | 3/1972 | Burghele et al. |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Arseneault et al. |
| 4,308,868 A | 1/1982 | Jhabvala |

(Continued)

FOREIGN PATENT DOCUMENTS

DE 19750043 5/1999

(Continued)

OTHER PUBLICATIONS

Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).

(Continued)

*Primary Examiner* — Carl H Layno
*Assistant Examiner* — Natasha N Patel
(74) *Attorney, Agent, or Firm* — Melissa Acosta; Christopher S. L. Crawford; Peter Lando

(57) ABSTRACT

Methods and systems for treating movement disorders are disclosed. A method in accordance with one embodiment can include determining that the movement disorder affects the patient's gait, oral functioning, and/or other functioning, and applying electrical stimulation proximate to the interhemispheric fissure, the Sylvian fissure, or between the two fissures, respectively. In another embodiment, the method can include selecting at least one neural process from among a plurality of processes sequentially carried out by a patient to cause a muscle movement in the patient (e.g., a planning process, an initiation process, and an execution process), and applying electrical stimulation to a location of the patient's brain associated with the at least one neural process.

10 Claims, 4 Drawing Sheets

U.S. PATENT DOCUMENTS

| | | | |
|---|---|---|---|
| 4,328,813 A | 5/1982 | Ray | |
| 4,340,038 A | 7/1982 | McKean | |
| 4,431,000 A | 2/1984 | Butler et al. | |
| 4,474,186 A | 10/1984 | Ledley et al. | |
| 4,542,752 A | 9/1985 | Dehaan et al. | |
| 4,590,946 A | 5/1986 | Loeb | |
| 4,607,639 A | 8/1986 | Tanagho et al. | |
| 4,646,744 A | 3/1987 | Capel | |
| 4,702,254 A | 10/1987 | Zabara | |
| 4,844,075 A | 7/1989 | Liss et al. | |
| 4,865,048 A | 9/1989 | Eckerson | |
| 4,869,255 A | 9/1989 | Putz | |
| 4,903,702 A | 2/1990 | Putz | |
| 4,969,468 A | 11/1990 | Byers et al. | |
| 5,002,053 A | 3/1991 | Garcia-Rill et al. | |
| 5,024,226 A | 6/1991 | Tan | |
| 5,031,618 A | 7/1991 | Mullett | |
| 5,044,368 A | 9/1991 | Putz | |
| 5,054,906 A | 10/1991 | Lyons, Jr. | |
| 5,063,932 A | 11/1991 | Dahl et al. | |
| 5,092,835 A | 3/1992 | Schurig et al. | |
| 5,121,754 A | 6/1992 | Mullett | |
| 5,143,089 A | 9/1992 | Alt | |
| 5,169,384 A | 12/1992 | Bosniak et al. | |
| 5,184,620 A | 2/1993 | Cudahy et al. | |
| 5,193,540 A | 3/1993 | Schulman et al. | |
| 5,215,086 A | 6/1993 | Terry, Jr. et al. | |
| 5,215,088 A | 6/1993 | Normann et al. | |
| 5,224,491 A | 7/1993 | Mehra | |
| 5,255,678 A | 10/1993 | Deslauriers et al. | |
| 5,263,967 A | 11/1993 | Lyons, III et al. | |
| 5,271,417 A | 12/1993 | Swanson et al. | |
| 5,282,468 A | 2/1994 | Klepinski | |
| 5,299,569 A | 4/1994 | Wernicke et al. | |
| 5,303,705 A | 4/1994 | Nenov | |
| 5,304,206 A | 4/1994 | Baker, Jr. et al. | |
| 5,314,458 A | 5/1994 | Najafi et al. | |
| 5,358,513 A | 10/1994 | Powell, III et al. | |
| 5,370,672 A | 12/1994 | Fowler et al. | |
| 5,405,375 A | 4/1995 | Ayers et al. | |
| 5,406,957 A | 4/1995 | Tansey | |
| 5,411,540 A | 5/1995 | Edell et al. | |
| 5,417,719 A | 5/1995 | Hull et al. | |
| 5,423,864 A | 6/1995 | Ljungstroem | |
| 5,441,528 A | 8/1995 | Chang et al. | |
| 5,464,446 A | 11/1995 | Dreessen et al. | |
| 5,520,190 A | 5/1996 | Benedict et al. | |
| 5,522,864 A | 6/1996 | Wallace et al. | |
| 5,537,512 A | 7/1996 | Hsia et al. | |
| 5,540,734 A | 7/1996 | Zabara | |
| 5,540,736 A | 7/1996 | Haimovich et al. | |
| 5,549,655 A | 8/1996 | Erickson | |
| 5,562,708 A | 10/1996 | Combs et al. | |
| 5,575,813 A | 11/1996 | Edell et al. | |
| 5,591,216 A | 1/1997 | Testerman et al. | |
| 5,593,432 A | 1/1997 | Crowther | |
| 5,601,611 A | 2/1997 | Fayram et al. | |
| 5,611,350 A | 3/1997 | John | |
| 5,618,531 A | 4/1997 | Cherksey | |
| 5,628,317 A | 5/1997 | Starkebaum et al. | |
| 5,674,251 A | 10/1997 | Combs et al. | |
| 5,676,655 A | 10/1997 | Howard, III et al. | |
| 5,683,422 A | 11/1997 | Rise | |
| 5,702,429 A | 12/1997 | King | |
| 5,707,334 A | 1/1998 | Young | |
| 5,711,316 A | 1/1998 | Elsberry et al. | |
| 5,713,922 A | 2/1998 | King | |
| 5,713,923 A | 2/1998 | Ward et al. | |
| 5,716,377 A | 2/1998 | Rise et al. | |
| 5,722,401 A | 3/1998 | Pietroski et al. | |
| 5,735,814 A | 4/1998 | Elsberry et al. | |
| 5,750,376 A | 5/1998 | Weiss et al. | |
| 5,752,979 A | 5/1998 | Benabid | |
| 5,769,778 A | 6/1998 | Abrams et al. | |
| 5,772,591 A | 6/1998 | Cram | |
| 5,782,798 A | 7/1998 | Rise | |
| 5,782,873 A | 7/1998 | Collins | |
| 5,792,186 A | 8/1998 | Rise | |
| 5,797,970 A | 8/1998 | Pouvreau | |
| 5,814,014 A | 9/1998 | Elsberry et al. | |
| 5,814,092 A | 9/1998 | King | |
| 5,824,021 A | 10/1998 | Rise | |
| 5,824,030 A | 10/1998 | Yang et al. | |
| 5,832,932 A | 11/1998 | Elsberry et al. | |
| 5,833,709 A | 11/1998 | Rise et al. | |
| 5,843,148 A | 12/1998 | Gijsbers et al. | |
| 5,843,150 A | 12/1998 | Dreessen et al. | |
| 5,865,842 A | 2/1999 | Knuth et al. | |
| 5,871,517 A | 2/1999 | Abrams et al. | |
| 5,885,976 A | 3/1999 | Sandyk | |
| 5,886,769 A | 3/1999 | Zolten | |
| 5,893,883 A | 4/1999 | Torgerson et al. | |
| 5,904,916 A | 5/1999 | Hirsch | |
| 5,913,882 A | 6/1999 | King | |
| 5,916,171 A | 6/1999 | Mayevsky | |
| 5,925,070 A | 7/1999 | King et al. | |
| 5,928,144 A | 7/1999 | Real | |
| 5,938,688 A | 8/1999 | Schiff | |
| 5,938,689 A | 8/1999 | Fischell et al. | |
| 5,941,906 A | 8/1999 | Barreras, Sr. et al. | |
| 5,964,794 A | 10/1999 | Bolz et al. | |
| 5,975,085 A | 11/1999 | Rise | |
| 5,978,702 A | 11/1999 | Ward et al. | |
| 5,983,140 A | 11/1999 | Smith et al. | |
| 6,006,124 A | 12/1999 | Fischell et al. | |
| 6,011,996 A | 1/2000 | Gielen et al. | |
| 6,016,449 A | 1/2000 | Fischell et al. | |
| 6,018,682 A | 1/2000 | Rise | |
| 6,021,352 A | 2/2000 | Christopherson et al. | |
| 6,026,326 A | 2/2000 | Bardy | |
| 6,035,236 A | 3/2000 | Jarding et al. | |
| 6,040,180 A | 3/2000 | Johe | |
| 6,042,579 A | 3/2000 | Elsberry et al. | |
| 6,052,624 A | 4/2000 | Mann | |
| 6,055,456 A | 4/2000 | Gerber | |
| 6,057,846 A | 5/2000 | Sever, Jr. | |
| 6,057,847 A | 5/2000 | Jenkins | |
| 6,058,331 A | 5/2000 | King | |
| 6,060,048 A | 5/2000 | Cherksey | |
| 6,061,593 A | 5/2000 | Fischell et al. | |
| 6,066,163 A | 5/2000 | John | |
| 6,095,148 A | 8/2000 | Shastri et al. | |
| 6,104,956 A | 8/2000 | Naritoku et al. | |
| 6,104,960 A | 8/2000 | Duysens et al. | |
| 6,122,548 A | 9/2000 | Starkebaum et al. | |
| 6,126,657 A | 10/2000 | Edwards et al. | |
| 6,128,527 A | 10/2000 | Howard, III et al. | |
| 6,128,537 A | 10/2000 | Rise | |
| 6,128,538 A | 10/2000 | Fischell et al. | |
| 6,129,685 A * | 10/2000 | Howard, III | 600/585 |
| 6,134,474 A | 10/2000 | Fischell | |
| 6,152,143 A | 11/2000 | Edwards | |
| 6,161,044 A | 12/2000 | Silverstone | |
| 6,161,045 A | 12/2000 | Fischell et al. | |
| 6,176,242 B1 | 1/2001 | Rise | |
| 6,190,893 B1 | 2/2001 | Shastri et al. | |
| 6,198,958 B1 | 3/2001 | Ives et al. | |
| 6,205,360 B1 | 3/2001 | Carter et al. | |
| 6,210,417 B1 | 4/2001 | Baudino et al. | |
| 6,221,908 B1 | 4/2001 | Kilgard et al. | |
| 6,230,049 B1 | 5/2001 | Fischell et al. | |
| 6,236,892 B1 | 5/2001 | Feler | |
| 6,246,912 B1 | 6/2001 | Sluijter et al. | |
| 6,263,225 B1 | 7/2001 | Howard, III | |
| 6,280,462 B1 | 8/2001 | Hauser et al. | |
| 6,301,493 B1 | 10/2001 | Marro et al. | |
| 6,304,787 B1 | 10/2001 | Kuzma et al. | |
| 6,319,241 B1 | 11/2001 | King et al. | |
| 6,339,725 B1 | 1/2002 | Naritoku et al. | |
| 6,353,754 B1 | 3/2002 | Fischell | |
| 6,354,299 B1 | 3/2002 | Fischell | |
| 6,356,792 B1 | 3/2002 | Errico | |
| 6,360,122 B1 | 3/2002 | Fischell | |
| 6,366,813 B1 | 4/2002 | DiLorenzo | |
| 6,375,666 B1 | 4/2002 | Mische | |
| 6,405,079 B1 | 6/2002 | Ansarinia | |
| 6,418,344 B1 | 7/2002 | Rezai et al. | |

| | | |
|---|---|---|
| 6,427,086 B1 | 7/2002 | Fischell |
| 6,456,886 B1 | 9/2002 | Howard, III et al. |
| 6,459,936 B2 | 10/2002 | Fischell et al. |
| 6,463,328 B1 | 10/2002 | John |
| 6,464,356 B1 | 10/2002 | Sabel |
| 6,466,822 B1 | 10/2002 | Pless |
| 6,473,639 B1 | 10/2002 | Fischell |
| 6,480,743 B1 | 11/2002 | Kirkpatrick |
| 6,484,059 B2 | 11/2002 | Gielen |
| 6,487,450 B1 | 11/2002 | Chen |
| 6,499,488 B1 | 12/2002 | Hunter et al. |
| 6,503,187 B1 * | 1/2003 | Ilmoniemi et al. ............... 600/14 |
| 6,505,075 B1 | 1/2003 | Weiner |
| 6,507,755 B1 | 1/2003 | Gozani et al. |
| 6,529,774 B1 | 3/2003 | Greene |
| 6,539,263 B1 | 3/2003 | Schiff et al. |
| 6,549,814 B1 | 4/2003 | Strutz et al. |
| 6,556,868 B2 | 4/2003 | Naritoku et al. |
| 6,569,654 B2 | 5/2003 | Shastri et al. |
| 6,591,138 B1 | 7/2003 | Fischell et al. |
| 6,597,954 B1 | 7/2003 | Pless et al. |
| 6,615,065 B1 | 9/2003 | Barrett et al. |
| 6,622,048 B1 | 9/2003 | Mann |
| 6,633,780 B1 | 10/2003 | Berger |
| 6,647,296 B2 | 11/2003 | Fischell et al. |
| 6,658,299 B1 | 12/2003 | Dobelle |
| 6,665,562 B2 | 12/2003 | Gluckman et al. |
| 6,684,105 B2 | 1/2004 | Cohen et al. |
| 6,687,525 B2 | 2/2004 | Llinas et al. |
| 6,690,974 B2 | 2/2004 | Archer et al. |
| 6,708,064 B2 * | 3/2004 | Rezai ............................... 607/45 |
| 6,725,094 B2 | 4/2004 | Saberski |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,944,501 B1 | 9/2005 | Pless |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,107,097 B2 | 9/2006 | Stern et al. |
| 7,110,820 B2 | 9/2006 | Tcheng et al. |
| 7,184,840 B2 | 2/2007 | Stolz et al. |
| 2002/0091419 A1 | 7/2002 | Firlik et al. |
| 2002/0099412 A1 | 7/2002 | Fischell |
| 2002/0138101 A1 | 9/2002 | Suda et al. |
| 2002/0169485 A1 | 11/2002 | Pless |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2003/0195602 A1 | 10/2003 | Boling |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | DeCharms |
| 2004/0102828 A1 | 5/2004 | Lowry et al. |
| 2004/0111127 A1 * | 6/2004 | Gliner ............................... 607/45 |
| 2004/0131998 A1 | 7/2004 | Marom et al. |
| 2004/0138550 A1 | 7/2004 | Hartlep et al. |
| 2004/0158298 A1 | 8/2004 | Gliner et al. |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2007/0088403 A1 | 4/2007 | Wyler |

FOREIGN PATENT DOCUMENTS

| | | |
|---|---|---|
| EP | 0214527 | 3/1987 |
| EP | 0319844 | 6/1989 |
| EP | 0998958 | 10/2000 |
| EP | 1145736 | 10/2001 |
| EP | 1180056 | 11/2003 |
| WO | WO 87/07511 | 12/1987 |
| WO | WO 94/07564 | 12/1987 |
| WO | WO 95/21591 | 8/1995 |
| WO | WO 98/06342 | 2/1998 |
| WO | WO 01/97906 | 12/2001 |
| WO | WO 02/09811 | 2/2002 |
| WO | WO 02/36003 | 5/2002 |
| WO | WO 02/38031 | 5/2002 |
| WO | WO 02/38217 | 5/2002 |
| WO | WO 03/082402 | 3/2003 |
| WO | WO 03/043690 | 5/2003 |

OTHER PUBLICATIONS

Barres, et al., "Proliferation of oligodendrocyte precursor cells depends on electrical activity in axons," Nature; Medical Research Council Developmental Neurobiology Programme, Department of Biology, University College, London, p. 258, (Jan. 21, 1993).

Behrens, T. et al., "Non-invasive mapping of connections between human thalamus and cortex using diffusion imaging," Nature neuroscience, vol. 6, No. 7, pp. 750-757, Jul. 2003.

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].

Bluestone, Avraham Y. et al., "Three-dimensional optical tomography of hemodynamics in the human head," Optics Express, vol. 9, No. 6, pp. 272-286 (Sep. 10, 2001).

Brain Electrical Stimulation to Enhance Recovery After Stroke. ClinicalTrials.gov. [Retrieved on Dec. 22, 2005]. Retrieved from the internet <URL http://www.clinicaltrials.gov/ct/show/NCT00085657?order=2>.

Burnett, Mark G. et al., "Diffuse optical measurement of blood flow, blood oxygenation, and metabolism in a human brain during sensorimotor cortex activation," Optics Letters, vol. 29, No. 15, pp: 1766-1768 (Aug. 1, 2004).

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL: http://www.mcmaster.ca.inabis98/schallert/bury0827/index.html>.

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation afor Advanced Parkinson's Disease: Case Report," Movement Disorders, 15(1):169-171,2000.

Canavero, S. and Paolotti, R., "Extradural Motor Cortex Stimulation for Advanced Parkinson's Disease: Case Report," Movement Disorders 15(1): 160-171, 2000.

Cao, Yue et al., "Cortical Language Activation in Stroke Patients Recovering From Aphasia With Functional MRI," Stroke, vol. 30, pp. 2331-2340, Nov. 1999.

Cheun et al., "Differentiation of a Stem Cell Line Toward a Neuronal Phenotype," Int. J. Devl. Neuroscience, vol. 9, No. 4, pp. 391-404 (1991).

Cincotta et al., "Reorganization of the motor cortex in a patient with congenital hemiparesis and mirror movements," Neurology, vol. 55, pp. 129-131 (2000).

Classen, et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer, S.C. and Bastings, E.P., "Mapping clinically relevant plasticity after stroke," Neuropharmacology vol. 19, No. 5, pp. 842-851 (Apr. 2000).

Cytokines Web Clinical Significance. Cytokines Web, 2 pages. [Retrieved on Sep. 2, 2005]. Retrieved from the internet: <URL: <http://cmbi.bjmu.edu.cn/cmbidata/cgf/CGF_Database/cytweb/roles/index.html.

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppressess specific excitatory circuits in the human motor cortex," Physiology in Press; published online on Apr. 21, 2005 as 10.1113/jphysio.2005.087288.

Ding, Yuemin et al., "Neural Plasticity After Spinal Cord Injury," Current Pharmaceutical Design vol. 11, No. 11, pp. 1441-1450, Abstract Only- 1 page (Apr. 2005).

Duncan, Pamela W. et al., "Defining post-stroke recovery: implications for design and interpretation of drug trials," Neuropharmacology vol. 39, pp. 835-841 (2000).

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Hayakawa, Toshiji et al., "Changes in Cerebral Oxygenation and Hemodynamics During Obstructive Sleep Apneas," Chest, vol. 109, pp. 916-921 (1996).

Hodge, Jr., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., 1 page [Retrieved on Oct. 14, 2005]. Retrieved from the internet: <URL http://www.iss.com/Products/imagent_fmri.html>.

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilled motor function in chronic stroke," Brain Advance Access, Jan. 5, 2005, pp. 1-10, Brain.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent™.pdf>.

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domans and Determinants of Quality of Life After Stroke Caused by Brian Infarction," Arch. Phys. Med. Rehabil., vol. 81, pp. 1541-1546 (Dec. 2000).

Keyvani, Kathy et al., "Suppression of proteasome C2 contralateral to ischemic lesions in rat brain," Brain Research, vol. 858, pp. 386-392, 2000.

Kilgard, Michael et al., "Cortical Map Reorganization Enabled by Nucleus Basalis Activity," Science, vol. 279, pp. 1714-1717 (Mar. 13, 1998).

Kopell et al., "The Continuing Evolution of Psychiatric Neurosurgery," CNS Spectrums, vol. 5, No. 10, pp. 20-31 (Oct. 2000).

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-Dopa dyskinesias. BioChemistry of PD. [Retrieved on Dec. 22, 2005]. Retrieved from the internet <URL http://www.mayo.edu/fdp/pd-info/dyskinesias.htm>.

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G., et al., "A sham stimulation-controlled trial of rTMS of the unaffected hemisphere in stroke patients," Neurology, vol. 64, pp. 1802-1804 (2005).

Martin et al, "Transcranial Magnetic Stimulation as a Complementary Treatment for Aphasia," Semin Speech Language, vol. 25, pp. 181-191 (2004) Abstract Only- 1 page.

Martinez et al., "Motor hand recovery after stroke Prognostic yield of early transcranial magnetic stimulation," Electromyography. Clin. Neurophysiology, vol. 39, pp. 405-410 (1999).

Meyerson, B.A. et al., "Motor Cortex Stimulation as Treatment of Trigeminal Neuropathic Pain", Acta Neurochirurgica Supplementum, vol. 58, pp. 150-153 (1993).

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al., "Level of action of cathodal DC polarisation induced inhibition of the human motor cortex," Dec. 2, 2002, Clinical Neurophysiology 114 (2003) 600-604.

Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nudo, Randolph J., et al., "Recovery after damage to motor cortical areas," Current Opinion in Neurobiology, vol. 9, Issue 6, pp. 740-747, Dec. 1, 1999.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," [Retrieved on Dec. 22, 2005]. Retrieved from the internet <URL <http://www.public.asu.edu/~tmcdani/publications.htm>>.

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity," Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Pearson, Helen, "Shock tactics for new neurons—Electricity may trigger nerve growth.", http://www.nature.com/nsu/010315/010315-8.html, (Mar. 14, 2001), 2 pgs, Nature News Service, Macmillan Magazines Ltd 2001.

Penn, Michael, "Stemming Parkinson's," on Wisconsin Alumni Magazine, Summer 2003, [Retrieved on Dec. 22, 2005]. Retrieved from the internet <URL http://www.uwalumni.com/onwisconsin/2003_summer/research.html>.

Penn, Michael, "Stemming Parkinson's," On Wisconsin Alumni Magazine, Summer 2003, [Retrieved on Dec. 22, 2005]. Retrieved from the internet <URL http://www.uwalumni.com/onwisconsin/2003_summer/research.html>.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annu. Rev. Neurosci. 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

SCIRun. Scientific Computing and Imaging Institute, 2 pages. [Retrieved on Jul. 24, 2005]. Retrieved from the internet: <URL: <http://sofware.sci.utah.edu/scirun.html>>.

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Stefan et al., "Introduction of plasticity in the human motor cortex by paired associative stimulation," Brian, vol. 123, No. 3, pp. 575-584 (Mar. 2000).

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The Ipsilateral Human Motor Cortex Can Functionally Compensate for Acute Contralateral Motor Cortex Dysfunction, " Current Biology, vol. 13, pp. 1201-1205, Jul. 15, 2003.

Taga, Gentaro et al., "Brain imaging in awake infants by near-infrared optical topography," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]. Retrieved from the internet <URL <http://www.somanetics.net/invos.htm>>.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Tsubokawa, T. et al., "Chronic Motor Cortex Stimulation for the Treatement of Central Pain", Acta Neurochirurgica Supplementum, vol. 52, pp. 137-139 (1991).

Tsubokawa, T. et al., "Treatment of Thalamic Pain by Chronic Motor Cortex Stimilation", PACE, vol. 14, pp. 131-134 (Jan. 1991).

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98, No. 20, pp. 11697-11701, Sep. 25, 2001.

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience, vol. 18, pp. 1115-1123 (Feb. 1998).

Bezard et al., "Cortical Stimulation and Epileptic Seizure: A Study of the Potential Risk in Primates," Neurosurgery, vol. 45, No. 2, Aug. 1999, 346-350.

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Cramer et al., "Use of Functional MRI to Guide Decisions in a clinical Stroke Trial," Stroke, Journal of the American Heart Association, May 2005, pp. e50-e52, American Heart Association, Dallas TX.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Haglund, Michael M. et al., "Optical imaging of epileptiform and functional activity in human cerebral cortex," Nature, Aug. 20, 1992, pp. 668-671, vol. 358, 1992 Nature Publishing Group.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Misawa et al., "Low-frequency transcranial magnetic stimulation for epilepsia partialis continua due to cortical dysplasia," Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Sioutos et al. Continuous Regional Cerebral Cortical Blood Flow Monitoring in Head-injured Patients, Neurosurgery, vol. 36, No. 5, May 1995, pp. 943-949.

The National Institutes of Health (NIH) Consensus Development Program, "Surgery for Epilepsy," National Institutes of Health Consensus Development conference Statement, Mar. 19-21, 1990, 16 pages.

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

U.S. Appl. No. 10/583,630, filed Jun. 20, 2006, Lozano.
U.S. Appl. No. 11/254,060, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/583,349, filed Oct. 18, 2006, Sloan.
U.S. Appl. No. 11/683,326, filed Dec. 12, 2006, Gliner et al.
U.S. Appl. No. 11/697,694, filed Apr. 6, 2007, Fowler.
U.S. Appl. No. 11/697,696, filed Apr. 6, 2007, Pascual-Leone.
U.S. Appl. No. 11/697,703, filed Apr. 6, 2007, Gaw.

Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.

Binder, J. M.D., "Functional Magnetic Resonance Imaging: Language Mapping," Neurosurgery Clinics of North America, vol. 8, No. 3, Jul. 1997, pp. 383-392.

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Kelly-Spratt, K. "Transfection of PC-12 cells: a model system for primary neuronal cells," Qiagen News, Customer application article, www.qiagen.com, Issue 4, 1998, 2 pages.

Kimura, K. et al., "Electrically induced neurite outgrowth of PC12 cells on the electrode surface," Published: Med. Biol. Eng. Comput., Jul. 1998, 36(4):493-8, http://www.ncbi.nlm.nih.gov/entrez/query.fcgi?db=pubmed&cmd=Retrieve&dopt=Abstract, Entrez PubMed Abstract, 1 page.

Mendonca, A.C., "Directly applied low intensity direct electric current enhances peripheral nerve regeneration in rats," Journal of Neuroscience Methods, 2003, vol. 129, pp. 183-190.

Politis, M. J., "Mammalian Optic Nerve Regeneration Following the Application of Electric Fields," The Journal of Trauma, Nov. 1988, Vol. 28, No. 11, pp. 1548-1552.

Schulz et al., "Localization of Epileptic Auras Induced on Stimulation by Subdural Electrodes," Epilepsia, Dec. 1997, vol. 38, Issue 12, pp. 1321-1329.

Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

\* cited by examiner

SYSTEMS AND METHODS FOR SELECTING STIMULATION SITES AND APPLYING TREATMENT, INCLUDING TREATMENT OF SYMPTOMS OF PARKINSON'S DISEASE, OTHER MOVEMENT DISORDERS, AND/OR DRUG SIDE EFFECTS

RELATED APPLICATIONS

This application is a division of 10/986,614, now U.S. Pat. No. 7,565,200, filed Nov. 12, 2004.

TECHNICAL FIELD

The present invention is directed generally toward systems and methods for selecting stimulation sites and treating symptoms of Parkinson's disease and other movement disorders, and/or drug side effects, for example, via electrical stimulation at the selected sites.

BACKGROUND

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex, the basal ganglia, the thalamus, and the motor cortex cooperatively interact to facilitate motor function control.

Many problems or abnormalities with body functions can be caused by damage, disease, and/or disorders in the brain. For example, Parkinson's Disease (PD) is related to the degeneration or death of dopamine producing neurons in the substantia nigra region of the basal ganglia in the brain. Dopamine is a neurotransmitter that transmits signals between areas of the brain. As the neurons in the substantia nigra deteriorate, the reduction in dopamine causes abnormal neural activity that results in a chronic, progressive deterioration of motor function control. Conservative estimates indicate that PD may affect more than one million individuals in the United States alone.

PD patients typically exhibit one or more of four primary symptoms. One primary symptom is a tremor in an extremity (e.g., a hand) that occurs while the extremity is at rest. Other primary symptoms include a generalized slowness of movement (bradykinesia); increased muscle rigidity or stiffness (rigidity); and gait or balance problems (postural dysfunction). In addition to or in lieu of these primary symptoms, PD patients may exhibit secondary symptoms including: difficulty initiating or resuming movements; loss of fine motor skills; lack of arm swing on the affected side of the body while walking; foot drag on the affected side of the body; decreased facial expression; voice and/or speech changes; cognitive disorders; feelings of depression or anxiety; and/or other symptoms.

Effectively treating PD or other movement disorders related to neurological conditions can be very difficult. Current treatments for PD symptoms include drugs, ablative surgical intervention, and/or neural stimulation. Drug treatments or therapies may involve, for example, the administration of a dopamine precursor that is converted to dopamine within the central nervous system (i.e., Levodopa (L-dopa)). Other types of drug therapies are also available. Unfortunately, drug therapies frequently become less effective or ineffective over time for an undesirably large patient population. A PD patient may require multiple drugs in combination to extend the time period of efficacy of drug therapies. Drug treatments additionally have a significant likelihood of inducing undesirable physical side effects; motor function complications such as uncontrollable involuntary movements (dyskinesias) are a particularly common side effect. Furthermore, drug treatments may induce undesirable cognitive side effects such as confusion and/or hallucinations.

Ablative surgical intervention for PD typically involves the destruction of one or more neural structures within the basal ganglia or thalamus that have become overactive because of the lack of dopamine. Unfortunately, such neural structures reside deep within the brain, and hence ablative surgical intervention is a very time consuming and highly invasive procedure. Potential complications associated with the procedure include risk of hemorrhage, stroke, and/or paralysis. Moreover, because PD is a progressive disease, multiple deep brain surgeries may be required as symptoms progressively worsen over time. Although ablative surgical intervention may improve a PD patient's motor function, it is not likely to completely restore normal motor function. Furthermore, since ablative surgical intervention permanently destroys neural tissue, the effects of such intervention cannot be readily adjusted or "fine tuned" over time.

Neural stimulation treatments have shown promising results for reducing some of the symptoms associated with PD. Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials in the event that the integration exceeds a threshold potential. A neural firing threshold, for example, may be approximately −55 mV. Action potentials propagate to the neuron's synapses and are then conveyed to other synaptically connected neurons.

Neural activity in the brain can be influenced by neural stimulation, which involves the application of electrical and/or magnetic stimuli to one or more target neural populations within a patient using a waveform generator or other type of device. Various neural functions can thus be promoted or disrupted by applying an electrical current to one or more regions of the brain. As a result, researchers have attempted to treat certain neurological conditions, including PD, using electrical or magnetic stimulation signals to control or affect brain functions.

Deep Brain Stimulation (DBS) is a stimulation therapy that has been used as an alternative to drug treatments and ablative surgical therapies. In DBS, one or more electrodes are surgically implanted into the brain proximate to deep brain or subcortical neural structures. For treating PD or other movement disorders, the electrodes are positioned in or proximate to the ventrointermediate nucleus of the thalamus; basal ganglia structures such as the globus pallidus internalis (GPi); or the Subthalamic Nucleus (STN). The location of the stimulation site for the electrodes depends upon the symptoms that a patient exhibits and the severity of the symptoms.

In a typical DBS system, a pulse generator delivers a continuous or essentially continuous electrical stimulation signal having a pulse repetition frequency of approximately 100 Hz to each of two deep brain electrodes. The electrodes are may be positioned bilaterally on the left and right sides of the brain relative to particular neural structures such as those indicated above. U.S. Pat. No. 5,883,709 discloses one conventional DBS system for treating movement disorders.

Although DBS therapies may significantly reduce one or more PD symptoms, particularly when combined with drug treatments, they are highly invasive procedures. In general, configuring a DBS system to properly function within a patient requires two time consuming, highly invasive surgical procedures for implanting the DBS electrodes. Each such surgical procedure has essentially the same risks as those described above for ablative surgical intervention. Moreover, DBS may not provide relief from some movement disorders.

Motor Cortex Stimulation (MCS) is another type of brain stimulation treatment that has been proposed for treating Parkinson's Disease. MCS involves the application of stimulation signals to the motor cortex of a patient. One MCS system includes a pulse generator connected to a strip electrode that is surgically implanted over a portion of only the motor cortex (precentral gyrus). The use of MCS to treat PD symptoms is described in Canavero, Sergio, *Extradural Motor Cortex Stimulation for Advanced Parkinson's Disease: Case Report*, Movement Disorders (Vol. 15, No. 1, 2000).

Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating PD symptoms. Present MCS techniques, however, fail to address or adequately consider a variety of factors that may enhance or optimize the extent to which a patient experiences short term and/or long term relief from PD symptoms.

DETAILED DESCRIPTION

Figure 1A:
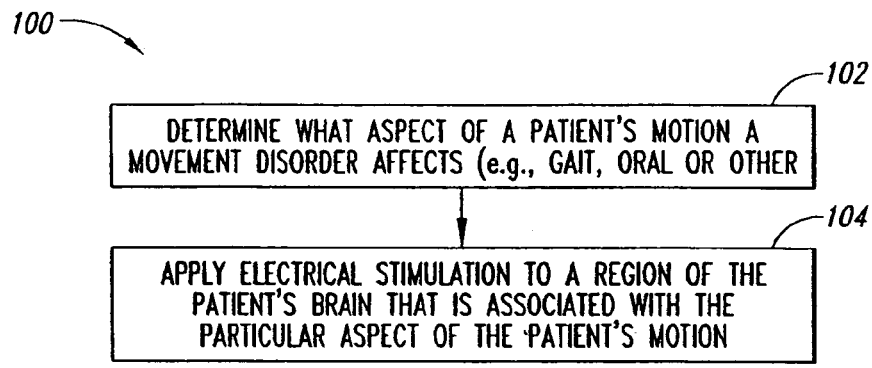
FIGS. 1A-1B are flow charts illustrating methods for treating movement disorders in accordance with an embodiment of the invention.

The following disclosure describes several embodiments of methods and systems for treating movement disorders (e.g., Parkinson's Disease (PD)) and/or associated symptoms, and/or symptoms associated with drug side effects, using cortical stimulation. Several methods and systems for applying treatment in accordance with embodiments of the invention are set forth and described in FIGS. 1A-7. It will be appreciated that other embodiments can include additional procedures and/or different features than those shown in FIGS. 1A-7. Additionally, methods and systems in accordance with several embodiments of the invention may not include all of the features shown in these Figures.

A method for treating movement disorders in accordance with one embodiment of the invention includes determining that the movement disorder affects a patient's gait, and applying electrical stimulation to a region of the patient's brain that is proximate to the interhemispheric fissure of the patient's brain. In another embodiment, the method can include determining that the movement disorder affects the patient's oral functioning, and can further include applying electrical stimulation to a region of the patient's brain that is proximate to the Sylvian fissure of the patient's brain. In still another embodiment, the method can include determining that the movement disorder affects an aspect of the patient's movement other than the patient's gait and oral functioning, and can further include applying electrical stimulation to a region of the patient's brain that is located between the interhemispheric fissure and the Sylvian fissure of the patient's brain.

Methods in accordance with further aspects of the invention can further include applying electrical stimulation to both sides of the central sulcus of the patient's brain, or on a single side of the central sulcus of the patient's brain. Stimulation can be applied ipsilaterally or contralaterally, in a unipolar manner, and/or in a bipolar manner.

In a still a further aspect of the invention, a method for treating movement disorders includes selecting at least one neural process from among a plurality of processes sequentially carried out by a patient to cause a muscle movement in the patient. The method can further include applying electrical stimulation to a location of the patient's brain associated with the at least one neural process. For example, the method can include selecting the at least one neural process from among a planning process, an initiation process, and an execution process. The method can further include applying electrical stimulation to the patient's dorsolateral prefrontal cortex, interhemispheric fissure, primary motor strip, or premotor cortex of the patient's brain.

In yet another embodiment, electrical stimulation can be used to address aspects of a patient's functioning that are attributed to drug intake (e.g., drug side effects). A method in accordance with one such embodiment includes determining what aspect of a patient's functioning is affected by the patient's drug intake, and applying electrical stimulation to a region of the brain that is associated with the aspect of the patient's functioning. In particular embodiments, this method can be used to address cognitive and/or motor dysfunctions resulting as side effects from the patient's intake of drugs that target Parkinson's disease and/or other movement disorders.

FIG. 1A is a block diagram illustrating a method 100 for treating a patient's movement disorder(s) and/or associated symptoms. The movement disorder may be associated with Parkinson's disease (PD) and/or other conditions, including other pathological conditions. In process portion 102, the method 100 includes determining what aspect of a patient's motion the movement disorder affects. For example, the movement disorder may primarily affect the patient's gait, or the patient's oral functions, (e.g., the patient's speech, chewing, and/or swallowing activities). Other patients may have other aspects of their motion affected. For example, other patients may experience tremors at an extremity, and/or difficulties with arm movement, and/or midline symptoms, including difficulties with postural stability. Most, if not all, of the foregoing symptoms can be diagnosed and distinguished from each other in a relatively straightforward manner using clinical examinations and/or patient reports.

In process portion 104, the method 100 includes applying electrical stimulation to a region of the patient's brain that is associated with the particular aspect of the patient's motion identified in process portion 102. In particular, different parts of the brain may be associated with different aspects of the patient's movements, and the method 100 can include stimulating or preferentially stimulating those areas most closely associated with the particular symptoms experienced by the patient. Further details of the brain areas that can be stimulated in accordance with embodiments of the invention are described below with reference to FIG. 1B.

Figure 1B:
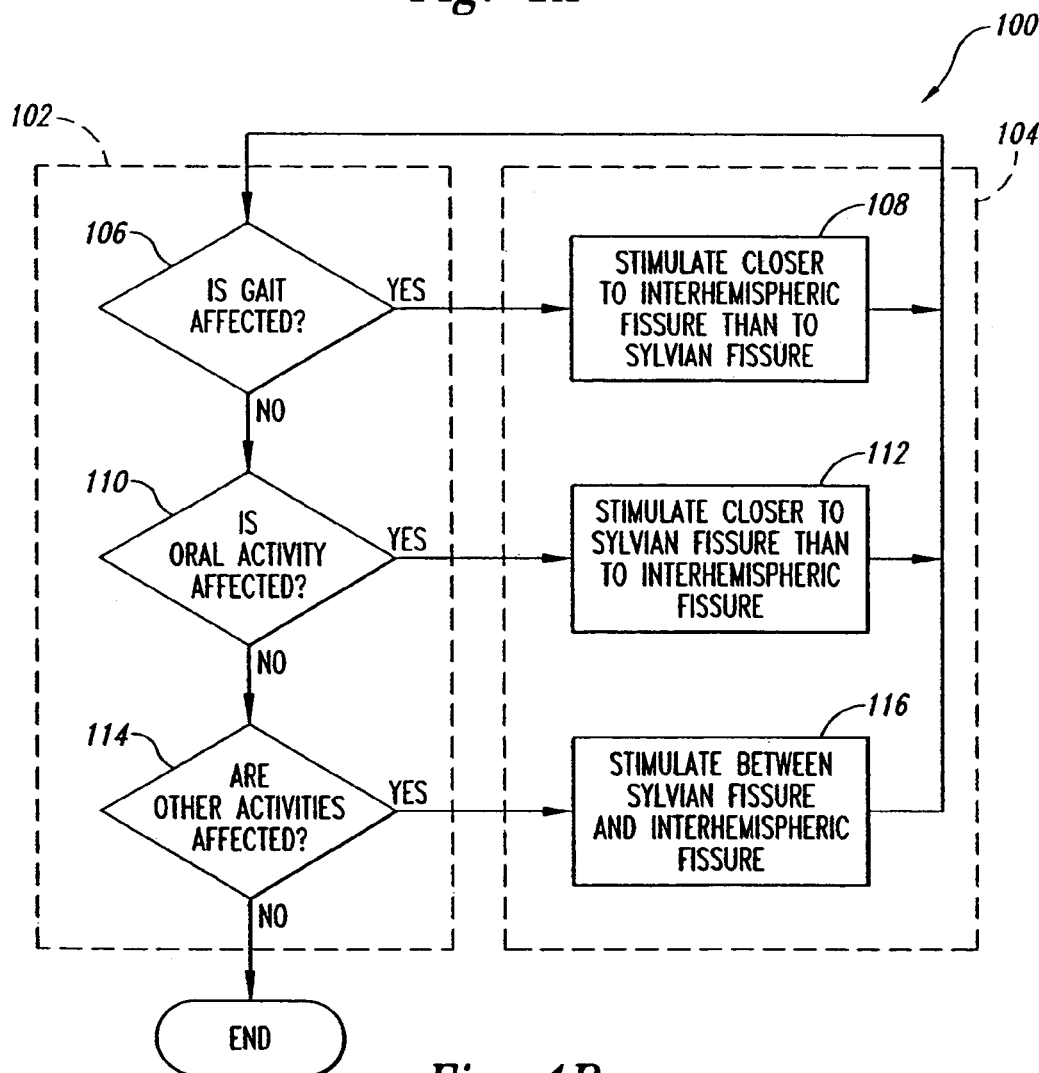

Referring now to FIG. 1B, process portion 102 can include determining whether or not the patient's gait is affected (process portion 106) and, if it is, stimulating the patient's brain closer to the interhemispheric fissure than to the Sylvian fissure (process portion 108). In process portion 110, the process 100 can include determining if the patient's oral activity is affected and, if it is, stimulating the patient's brain closer to the Sylvian fissure than to the interhemispheric fissure (process portion 112). If a practitioner determines that activities other than the patient's gait and oral functions are affected (process portion 114), the practitioner can stimulate the patient's brain between the Sylvian fissure and the interhemispheric fissure, with a reduced preference for proximity to either fissure.

Figure 1C:
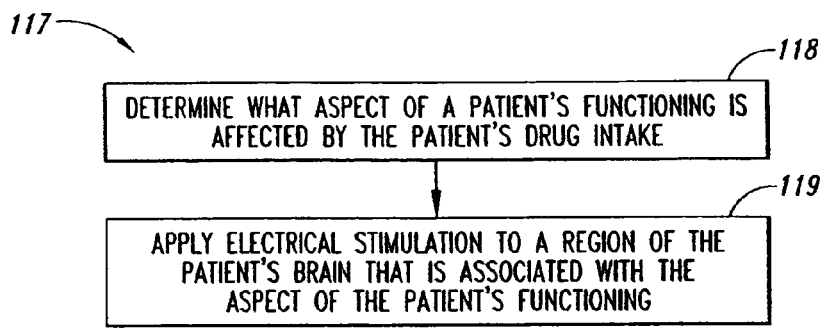
FIG. 1C is a flow chart illustrating a method for treating drug side effects, in accordance with another embodiment of the invention.

In other embodiments, methods similar in part to those described above with reference to FIGS. 1A and 1B can be used to address additional and/or other types of symptoms. For example, FIG. 1C illustrates a process 117 that includes determining what aspect of a patient's functioning is affected by the patient's chemical substance or drug intake (process portion 118). The process can further include applying electrical stimulation to one or more regions of the patient's brain that are associated with the aspect of the patient's functioning (process portion 119).

In further particular examples, the drug or drugs taken by the patient can include drugs taken to address movement disorders (e.g., PD) but that have side effects on the patient's cognitive and/or motor functioning. L-dopa is one such drug that can induce unwanted dyskinesias (e.g., chorea and/or dystonia). The dyskinesias can include peak-doses dyskinesias (associated with peak levels of L-dopa in the brain), "off" dyskinesias (which occurs when the effects of L-dopa wear off), and/or diphasic dyskinesias (associated with changes in the plasma level of L-dopa, typically at the beginning and/or end of a dose). Other drugs or chemical substances that may produce unwanted side effects can include Sinemet, Mirapex and glial-derived neurotrophic factor (GDNF).

The site(s) of the patient's brain selected for stimulation can depend on the aspects of the patient's functioning to be addressed. For example, if the effects of the drug are related to the patient's motion, the stimulation can be applied to the primary motor cortex, premotor cortex and/or supplemental motor area. If the effects relate to the patient's cognitive abilities, the stimulation can be applied to the prefrontal cortex. Illustrations of representative stimulation systems and stimulation sites associated with the foregoing method are described below with reference to FIGS. 2-4.

Figure 2:
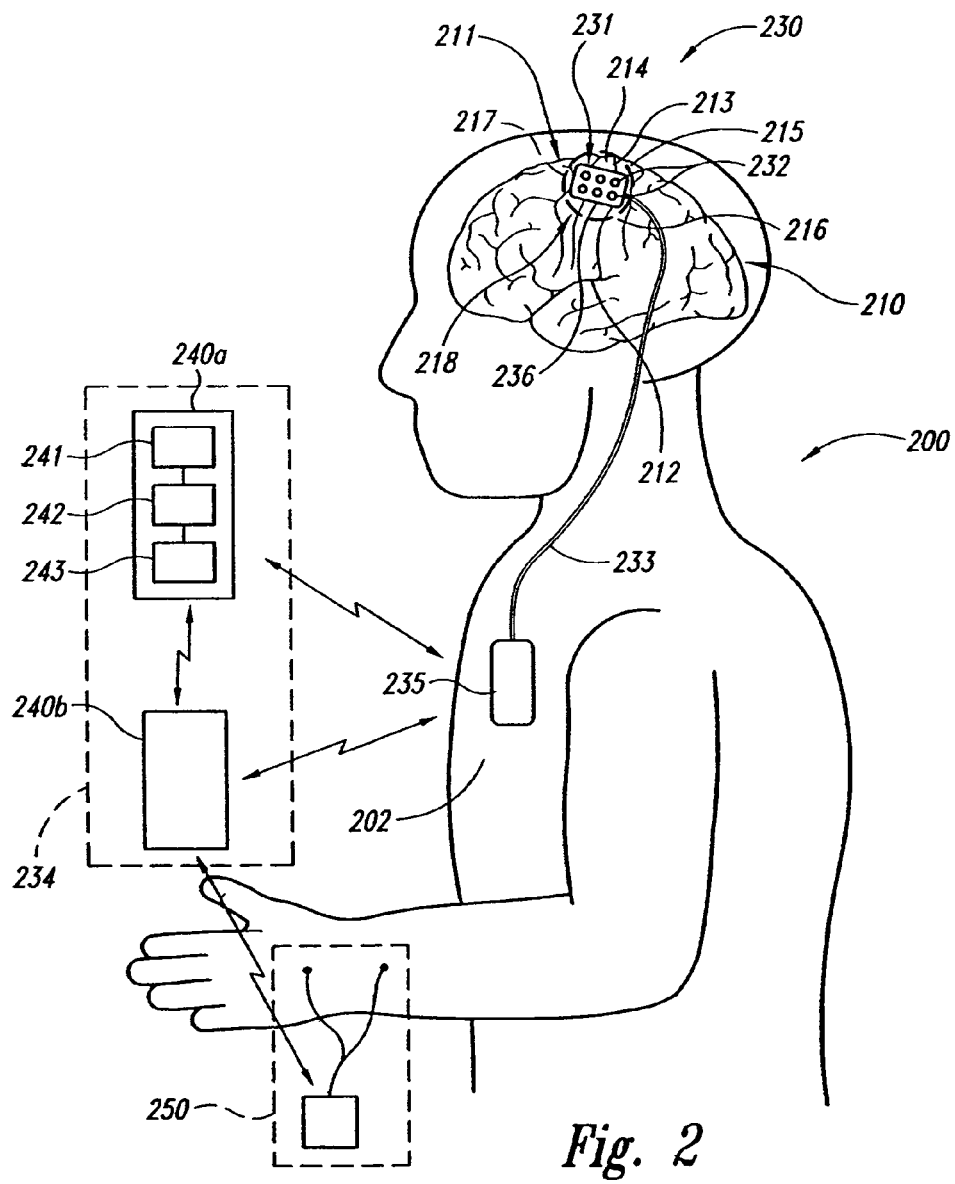
FIG. 2 is a partially schematic, left side illustration of a human brain indicating stimulation areas associated with addressing gait-related movement disorder symptoms in accordance with an embodiment of the invention.

FIG. 2 is a schematic illustration of a neural stimulation system 230 for treating symptoms of PD and/or other neurologic dysfunction (e.g., movement, cognitive and/or emotional dysfunction) in accordance with an embodiment of the invention. The neural stimulation system 230 can include a pulse generator 235 configured to deliver stimulation signals to a patient 200 via one or more electrode devices 231 implanted in the patient 200. Accordingly, the pulse generator 235 can be coupled to the electrode device 231 by one or more leads 233. The pulse generator 235 may further be configured for wireless and/or wire-based communication with a control system 234, which can in turn include one or more controllers 240 (shown in FIG. 2 as a first controller 240a and a second controller 240b). Depending upon embodiment details, the system 230 may further include one or more patient monitoring units 250 configured to detect, monitor, indicate, measure, and/or assess the severity of particular types of patient symptoms or deficits. Further details of the foregoing system components are described below.

The electrode device 231 may include one or more electrically conductive contacts 232 carried by one or more substrates 236, for example, in a manner described in U.S. application Ser. No. 10/742,579, entitled "Methods and Apparatus for Applying Electrical Stimulation and Manufacturing Same," filed on Dec. 18, 2003, and incorporated herein by reference. The contacts 232 are configured to provide, deliver, and/or apply stimulation signals to particular cortical regions of the patient's brain 210 and/or neural populations synaptically connected and/or proximate thereto. The electrode device 231 may alternatively or additionally include one or more penetrating, depth, deep brain, and/or nerve cuff electrodes. One or more of the contacts 232 may be configured as a signal return contact (i.e., a contact that provides a current return path for electrical continuity), and may be positioned relative to a variety of locations within and/or upon the patient's body to facilitate unipolar stimulation. This function may also be provided by other structures (e.g., a housing or other portion of the electrode device 231). In another embodiment, one or more of the contacts 232 can be configured to provide bipolar signals (e.g., the return contact can be positioned at or proximate to the stimulation site).

The characteristics and/or placement of the electrode device 231 may depend upon the nature of patient's underlying disorder(s), functional deficit(s), and/or the type and/or severity of symptoms that the patient 200 experiences or exhibits. In a particular embodiment, one or more portions of the electrode device 231 may be surgically implanted to apply, deliver, and/or direct stimulation signals to target neural populations within the patient's brain, for example, in a manner identical, essentially identical, or analogous to that described in U.S. application Ser. No. 10/732,731, entitled "System and Method for Treating Parkinson's Disease and Other Movement Disorders," filed on Dec. 9, 2003, and/or U.S. application Ser. No. 09/802,808, filed on Mar. 8, 2001, both incorporated herein by reference.

The electrode device 231 receives stimulation signals from the pulse generator 235, which may include hardware and/or software for generating and outputting stimulation signals in accordance with internal instruction sequences and/or in response to control signals, commands, instructions, and/or other information received from the controller(s) 240. The pulse generator 235 may include a power supply and a pulse unit, a programmable computer medium, and a communication unit. The power supply may include a battery or other type of power storage device. The pulse unit may include circuitry for generating pulse sequences that may be defined or characterized in accordance with various stimulation signal parameters. Stimulation can be provided at a current of from between 2 and 20 milliamps and at a frequency of 0.5 Hz, 1-2 Hz, or higher. In some embodiments, a generally low frequency signal (e.g., from about 0.5-10 Hz) can result in longer lasting beneficial effects and/or greater relief from adverse symptoms. In some embodiments, it is also beneficial to have a "reset" period. For example, the patient can undergo stimulation for a period of seconds, minutes, hours or days, followed by a period of no stimulation (e.g., for a number of seconds, minutes or hours) before stimulation begins again.

In a particular embodiment, the frequency of the stimulation signal can be varied in a random, aperiodic manner centered, for example, at a mean frequency of 5 Hz. The voltage or amplitude of the signal can be constant or can be varied in a variety of manners, including random variation and/or occasional high amplitude bursts. The range of frequencies may focus on the lower frequency ranges (e.g., from 1-2 Hz) and, for biphasic pulses, the first phase pulse width can be varied. In particular embodiments, the frequency can be varied in a manner indicated to break up oscillatory patterns that may exist between cortical and subcortical structures. Such signal patterns have been associated with Parkinson's disease and may be associated with other movement disorders as well. Aspects of these patterns are described by Timmermann et al. in an article titled, "The Cerebral Oscillatory Network of Parkinsonian Resting Tremor" (Brain (2003), 126, 199-212), incorporated herein in its entirety by reference. Further aspects of applicable signal parameters are described in co-pending U.S. application Ser. No. 10/782, 526, filed Feb. 19, 2004 and incorporated herein in its entirety by reference.

Each element of the pulse generator 235 may be incorporated or embedded in a surgically implantable case or housing. Depending upon embodiment details, the pulse generator 235 may be surgically implanted in the patient 200 at a subclavicular location 202. Alternatively, the pulse generator 235 may be surgically implanted above the patient's neck, for example, in the patient's skull at a location posterior to the patient's ear and/or proximate to an electrode implantation site. A surgically formed tunnel or path may route the lead or leads 233 that couple the pulse generator 235 to the electrode device 231, in a manner understood by those skilled in the art. Additionally, one or more electrically conductive portions of the pulse generator case or housing may serve as a return electrode for electrical current.

The controllers 240 may comprise hardware and/or software configured to direct and/or manage the local operation of the pulse generator 235. For example, the controllers may be configured to communicate control signals, commands, instructions, parameter settings and/or ranges, and/or other information to the pulse generator 235. Accordingly, the controllers 240 may each include a processing unit 241, a programmable or other computer-readable medium 242, and a communications unit 243. The communications unit 243 may include a user interface that facilitates communication with devices external to the pulse generator 235, for example, through telemetric signal transfer. The computer-readable medium 242 may comprise hardware and/or memory resident software. The computer-readable medium 242 may store operational mode information and/or program instruction sequences that may be selected and/or specified by a practitioner. The pulse generator 235 may be configured to deliver stimulation signals to particular electrode devices 231 and/or to specific electrical contacts 232 of the electrode device 231 on a selective basis at any given time, e.g., in a manner identical, essentially identical, or analogous to that described in U.S. application Ser. No. 09/978,134, entitled "Systems and Methods for Automatically Optimizing Stimulation Parameters and Electrode Configurations for Neuro-Stimulators," filed on Oct. 15, 2001, and incorporated herein by reference.

The first controller 240a can include a "full functionality" controller, configured for operation by a medical professional. The second controller 240b can include a limited or "partial functionality" controller configured for operation by a patient. The second controller 240b may facilitate patient-based selection and/or adjustment of particular preprogrammed operating modes and/or neural stimulation settings. In some embodiments, the first and second controllers 240a, 240b may be configured for wire-based or wireless communication with each other. One or both of the controllers 240 may be configured to receive information from the pulse generator 235 (e.g., the overall status and/or performance level of the pulse generator 235). Communication between the control system 234 and the pulse generator 235 may facilitate or effectuate specification, selection, and/or identification of operational modes, instruction sequences, and/or procedures for treating one or more patient conditions, states, and/or symptoms associated with PD, other movement disorders, and/or other types of neurologic dysfunction in a variety of manners.

The patient monitoring unit 250 may be used to determine the effects of the stimulation signals provided by the controller(s) 240, the pulse generator 235, and the electrode device(s) 231. Accordingly, the patient monitoring unit can include any type of device configured to detect, monitor, indicate, estimate, characterize, measure, calculate, and/or assess neural pathway characteristics and/or the nature, level, intensity, magnitude and/or severity of one or more types of patient states, conditions, deficits, and/or symptoms associated with PD and/or other neurological dysfunctions. For example, a patient monitoring unit 250 may include a motion detection system configured to detect patient movement associated with tremor. A motion detection system may include light emitting and/or detecting devices and/or accelerometers coupled to particular patient extremities. In another example, the patient monitoring unit 250 includes an Electromyography (EMG) system that has one or more sets of surface or depth electrodes positioned relative to particular muscle groups for detecting electrical signals corresponding to muscle fiber innervation. In still another example, the patient monitoring unit 250 includes an Electroencephalography (EEG), an Electrocorticography (ECoG) system, and/or a Magnetoencephalography (MEG) system. In yet another embodiment, the patient monitoring unit 250 includes one or more electrode contacts 232 and, optionally, software and/or hardware (e.g., signal processing software and/or circuitry) within the pulse generator 235.

In other arrangements, the patient monitoring unit 250 includes a neural imaging system, for example, a Magnetic Resonance Imaging (MRI), a functional MRI (fMRI), a Positron Emission Tomography (PET), and/or other type of system. As another example, the patient monitoring unit 250 may include one or more electrodes and/or probes (e.g., cerebral bloodflow monitors) positioned upon, proximate, and/or within given target neural populations, and associated hardware and/or software for detecting, presenting, and/or analyzing signals received therefrom. Still further examples of patient monitoring units are described in co-pending U.S. application Ser. No. 10/782,526, previously incorporated herein by reference.

In addition to illustrating a representative stimulation system 230, FIG. 2 also illustrates a representative placement for the electrode device 231. The electrode device 231 shown in FIG. 2 is positioned to provide stimulation to a patient 200 experiencing a gait-related neural dysfunction symptom (e.g., foot dragging). In one aspect of this embodiment, the electrode device 231 is positioned at a selected region 217 of the brain 210 located closer to the interhemispheric fissure 211 (located behind the plane of FIG. 2) than to the Sylvian fissure 212. The contacts 232 of the electrode device 231 can be located at the precentral gyrus 214 and/or the postcentral gyrus 215. In some cases, it may be advantageous to position the electrode device 231 to span the central sulcus 213, allowing the practitioner to selectively stimulate either or both of the precentral gyrus 214 and the postcentral gyrus 215. In other cases, the electrode device 231 can be positioned to extend posterior to the post-central sulcus 216. In any of these cases, the contacts 232 can be positioned subdurally or epidurally, depending on which is most effective for the patient 200. The contacts 232 can be located ipsilaterally and/or contralaterally with regard to the side of the patient 200 exhibiting the targeted symptoms. In at least one embodiment (e.g., when the patient 200 exhibits gait-related symptoms on both sides of the body), the practitioner can identify the brain hemisphere primarily associated with the patient's speech, and then stimulate that hemisphere so as to reduce or even prevent speech-related symptoms while at the same time addressing gait-related symptoms.

The electrode device 231 can include a plurality of contacts 232 that provide stimulation at one or more stimulation sites 218. Accordingly, the practitioner can sequentially stimulate at a different site (a) when it is not clearly evident, except by trial, where stimulation is most effective, and/or (b) when the patient 200 benefits from stimulation at multiple sites. In the latter cases stimulation may also be applied simultaneously to multiple sites.

In one aspect of this embodiment, the contacts 232 can be arranged in a 2×3 array, and in other embodiments, the contacts 232 can be arranged in arrays having other dimensions, including a single row of contacts 232. Each contact 232 can have a surface area and spacing selected to provide stimulation in the desired fashion. For example, in one embodiment, the contacts 232 have a surface area of about 5 mm$^2$, and each contact 232 can be spaced apart from its nearest neighbor by about 2.5 mm. In other embodiments, the size of the contacts 232 and the spacing between the contacts 232 can be different.

In any of the foregoing embodiments, the electrical stimulation provided by the electrode device 231 can reduce and/or eliminate gait-related symptoms experienced by the patient 200. The electrical stimulation provided by the electrode device 231 can be selected by the practitioner to provide unipolar and/or bipolar stimulation. As used herein, unipolar stimulation refers generally to stimulation provided by one or more contacts proximate to a given stimulation site 218 while all the contacts 232 are at or near the same electrical potential. In this case, a return electrode or contact is provided at a site distal the stimulation site 218, for example, at the implanted pulse generator 235. Conversely, bipolar stimulation, as used herein, refers generally to stimulation provided by at least two contacts 232 positioned proximate to the stimulation site 218, with one of the contacts at a higher electrical potential than the other. Multiple contacts 232 can be arranged in bipolar pairs, with each pair including one contact 232 at a higher potential than its pair mate. The pulse control system 234 can be configured to provide both unipolar and bipolar stimulation signals to the electrode device 231. Accordingly, the same electrode device 231 and pulse control system 234 can be used for patients receiving bipolar and unipolar stimulation. Furthermore, the pulse control system 234 can be programmed or reprogrammed during treatment to switch between bipolar and unipolar stimulation, when this type of alternation provides or is expected to provide an additional benefit to the patient.

Figure 3:
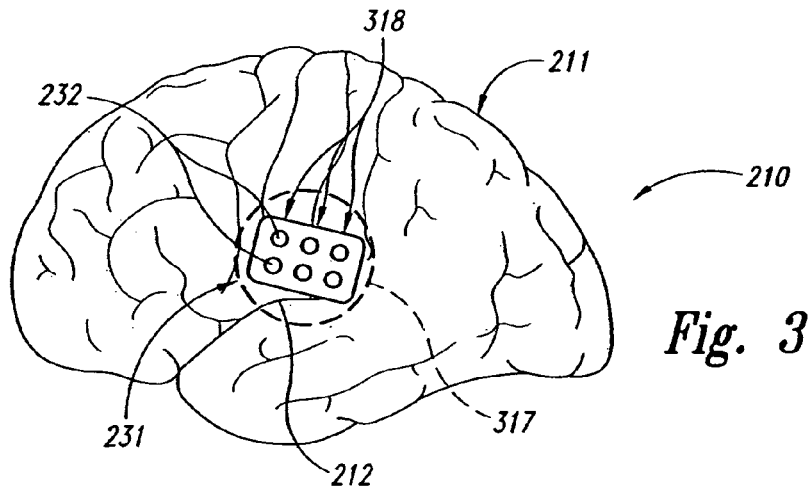
FIG. 3 is a partially schematic, left side illustration of the human brain indicating stimulation areas for addressing oral-related movement disorder symptoms, in accordance with another embodiment of the invention.

FIG. 3 is an illustration of the brain 210 with the electrode device 231 positioned at a selected region 317 to address oral-related movement disorder symptoms. Accordingly, the selected region 317 is positioned closer to the Sylvian fissure 212 than to the interhemispheric fissure 211. The contacts 232 can be located proximate to multiple stimulation sites 318, and can provide bipolar and/or unipolar stimulation, in a manner generally similar to that described above. As was also described above, the electrode device 231 can be sized, shaped and positioned in a manner that allows the practitioner to selectively stimulate multiple sites, sequentially and/or simultaneously. In one aspect of this embodiment, the electrode device 231 positioned at or near the Sylvian fissure 212 can have the same size and shape as the electrode device 231 positioned at or near the interhemispheric fissure 211 (FIG. 2). In other embodiments, the size and/or shape of the electrode device 231, and/or the arrangement of contacts 232 can be different depending on whether the electrode device 231 is selected to address primarily gait-related or oral-related symptoms.

Figure 4:
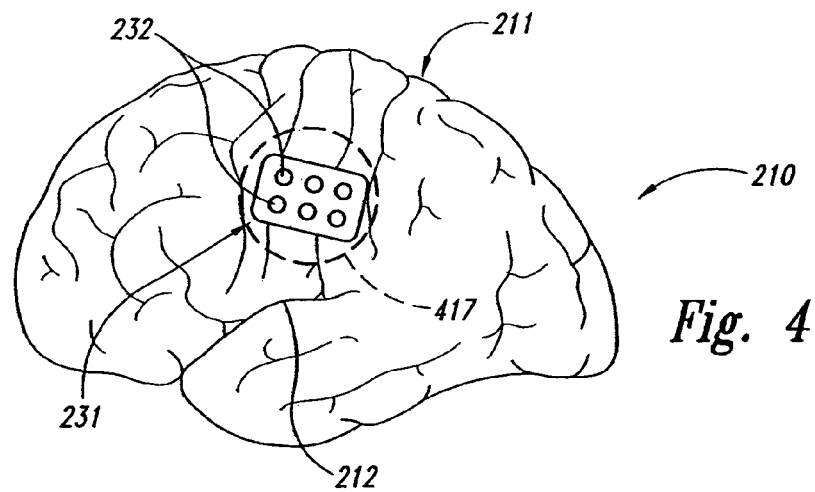
FIG. 4 is a partially schematic, left side illustration of the human brain illustrating stimulation locations for addressing movement disorder symptoms other than those related to a patient's gait and oral activity.

FIG. 4 is an illustration of the brain 210 with the electrode device 231 positioned at a selected region 417 to address symptoms other than gait-related symptoms and oral-related symptoms. Accordingly, the electrode device 231 can be positioned between the interhemispheric fissure 211 and the Sylvian fissure 212. In a particular aspect of this embodiment, the electrode device 231 and the contacts 232 it carries can be located approximately midway between the interhemispheric fissure 211 and the Sylvian fissure 212, and in other embodiments, the contacts 232 can be located more toward one fissure than the other. In any of these embodiments, the contacts 232 tend not to be located as close to the interhemispheric fissure 211 as was shown in FIG. 2, or as dose to the Sylvian fissure 212 as was shown in FIG. 3.

In still further embodiments, aspects of the arrangements described above with reference to FIGS. 2-4 can be combined. For example, if the patient 200 suffers from multiple symptoms (e.g., gait-related symptoms, oral-related symptoms and other symptoms), then a single electrode device 231 can be located over multiple selected regions. In another embodiment, the practitioner can implant multiple electrode devices 231 at each of the corresponding regions expected to provide aid to the patient 200. In either arrangement, the electrode(s) 231 expected to be necessary for addressing the patient's symptoms can be implanted in a single procedure, whether or not all the associated contacts 232 are ultimately used.

Figure 5:
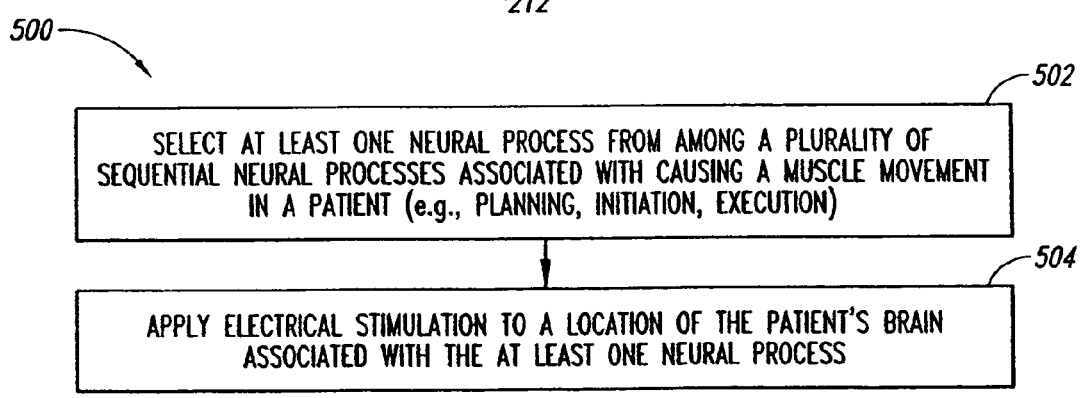
FIG. 5 is a flow chart illustrating a method for addressing dysfunction in sequentially-related processes associated with patient movement, in accordance with an embodiment of the invention.
Figure 6:
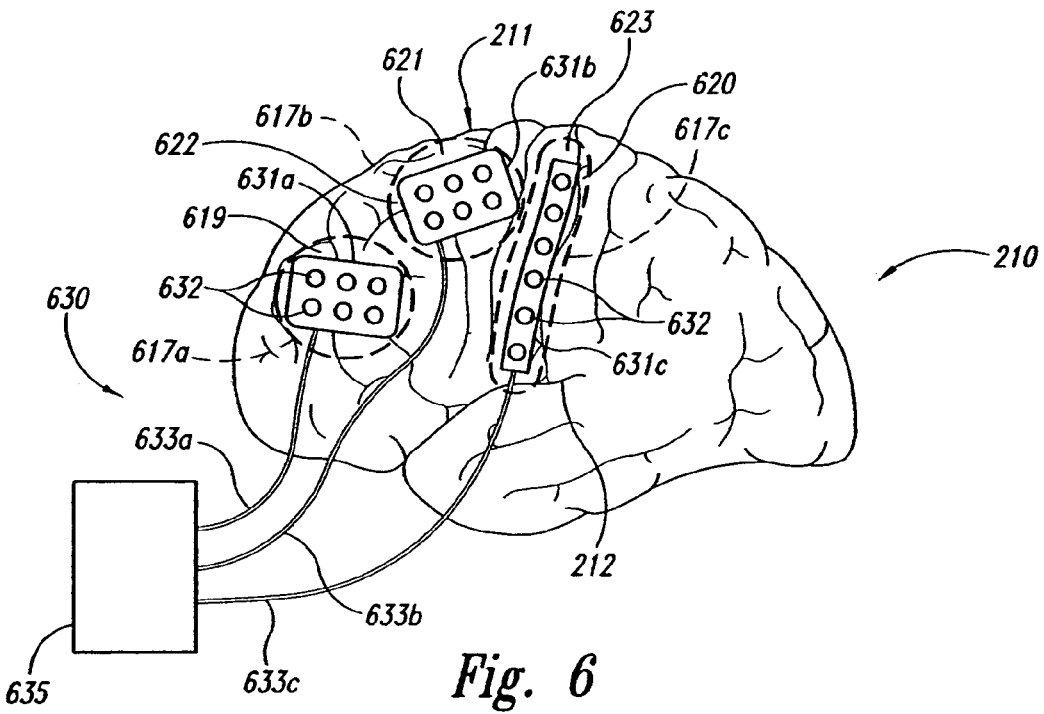
FIG. 6 is a partially schematic, left side illustration of the human brain illustrating sites at which electrical stimulation is provided to address dysfunctions associated with planning, initiating, and executing movements, in accordance with an embodiment of the invention.
Figure 7:
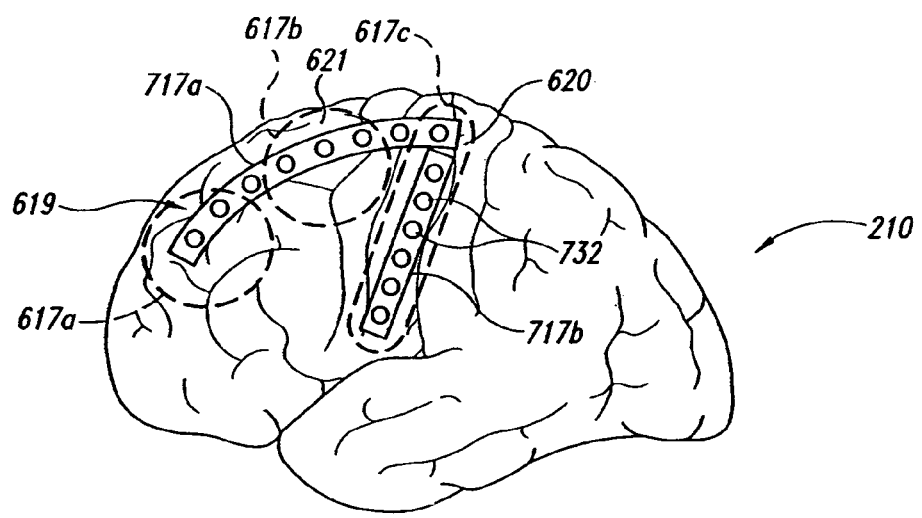
FIG. 7 is a left side illustration of the brain illustrating another arrangement of electrodes for stimulating brain regions associated with sequentially-related movement processes.

FIGS. 5-7 illustrate methods for applying electrical stimulation to a patient's brain in accordance with further aspects of the invention. Referring first to FIG. 5, a method 500 in accordance with one embodiment of the invention includes selecting at least one neural process from among a plurality of sequential neural processes associated with causing a muscle movement in the patient (block 502). The neural processes can include a planning process, an initiation process, and/or an execution process. As used herein, the planning process refers generally to the neurological process of forming instructions for carrying out a movement. Initiation refers generally to beginning the planned movement, and execution refers to fully carrying out the planned movement. Each movement executed by a patient generally results from the patient performing the foregoing three processes in sequence.

In block 504, electrical stimulation is applied to a location of the patient's brain associated with the at least one neural process selected in block 502. For example, in many cases, a different specific area of the brain is associated with each of the planning, initiation, and execution processes. Accordingly, the electrical stimulation can be applied to the location of the patients brain associated with one or more of the foregoing processes.

Once the (at least one) target neural process has been selected, the practitioner can implant an electrode device at least proximate to the area of the patient's brain associated with the target neural process. FIG. 6 illustrates the brain 210 along with three selected regions 617 (shown as a first selected region 617*a*, second selected region 617*b*, and third selected region 617*c*), each associated with one of the target neural processes. For example, the first selected region 617*a* can include the dorsal lateral prefrontal cortex 619, which has been shown to be associated with motor task planning. The second selected region 617*b* can include areas proximate to the interhemispheric fissure 211 and anterior to the motor strip 620 (e.g., the supplementary motor area 621). In a particular embodiment, the second selected region 617*b* can extend into the interhemispheric fissure 211. The third selected region 617*c* can include the motor strip 620 and can accordingly extend laterally from the interhemispheric fissure 211 to the Sylvian fissure 212. The third selected region 617*c* can also include the premotor cortex, a portion of the supplementary motor area 621. The motor strip 620 may be stimulated to address symptoms associated with fine motor control, and the premotor cortex may be stimulated to address symptoms associated with general motor control.

A stimulation system 630 for stimulating the brain 210 can include a pulse generator 635 coupled to one or more pulse control systems (not shown in FIG. 6) generally similar to those described above with reference to FIG. 2. In a particular embodiment in which it is desired to stimulate areas associated with all three neural processes (planning, initiation, and execution), the stimulation system 630 can include electrode devices 631 (shown as first, second, and third electrode devices 631*a*, 631*b*, and 631*c*, respectively) having electrical contacts 632 located at each of the three selected regions 617*a*-617*c*, respectively. When the second selected region 617*b* extends into the interhemispheric fissure 211, the second electrode device 631*b* can be placed in the interhemispheric fissure 211 as well. Alternatively, the second electrode device 631*b* can be located external, (but proximate to) the interhemispheric fissure 211, while still providing stimulation to neural structures located within the interhemispheric fissure 211, e.g., in a manner generally similar to that described in U.S. application Ser. No. 10/987,118, entitled "Electrode Configurations for Reducing Invasiveness and/or Enhancing Neural Stimulation Efficacy," filed concurrently herewith and incorporated herein by reference. Corresponding leads 633*a*-633*c* can be coupled between the pulse generator 635 and the electrode devices 631*a*-631*c*. In other embodiments, for example, when it is clear that only one or two of the regions 617*a*-617*c* would benefit from stimulation, fewer electrode devices 631 can be implanted in a single procedure at fewer than three regions.

Stimulation signals may be provided to the brain 210 in accordance with any of the parameters described above with reference to FIGS. 2-4. For example, the stimulation site can be located on the ipsilateral or contralateral side of the brain 210 with respect to the location of the impediment. In some embodiments, the practitioner can stimulate sites at both hemispheres, either sequentially or simultaneously, depending (for example) on the particular symptoms exhibited by the patient, and/or the particular process (e.g., planning, initiation, and/or execution) the practitioner wishes to address. The frequency, amplitude, pulse width and other signal parameters can also be varied in manners generally similar to those described above to provide effective treatment for the patient.

In some patients, a defect associated with one of the foregoing sequential processes may predominate. Once the defect associated with this process has been addressed, defects associated with other processes may become more evident. In other cases, it may be impossible or impracticable to identify which process is primarily responsible for the patient's symptoms, for example, because the processes are typically executed by the patient in very rapid succession. In any of these cases, the practitioner may implant multiple electrode devices and/or multiple contacts covering a range of target regions of the brain, and then stimulate a particular region until the problem with that region is addressed (or eliminated as a source of symptoms), then move to another region if symptoms associated with that region become evident, or if stimulation at the first region does not have the desired effect. Stimulation can be provided at multiple sites in a sequential, simultaneous, alternating, random, pseudorandom, and/or intermittent manner. The multiple electrode devices can be implanted simultaneously or serially (e.g., after stimulation with an initial electrode device has been completed or determined to be ineffective).

As described above with reference to FIG. 1C, stimulation can also be applied to the brain to address side effects associated with the patient's drug intake. Stimulation can be applied to the premotor cortex 622, the supplemental motor area 621, and/or the primary motor cortex 623 (for motion-related symptoms), and/or the prefrontal cortex 619 (for cognitive symptoms). The benefits of stimulation in these areas can include a reduction in drug side effects and/or a reduction in conventional drug doses (so as to produce essentially the same, the same, or greater therapeutic effect with fewer side effects). The patient may also have an increased "on time" (e.g., an increased period of time during which the drug is providing therapeutic effects) while exhibiting no side effects or reduced side effects.

FIG. 7 illustrates another arrangement of electrode devices that may be suitable for use when it is not certain which of the foregoing processes the patient has the most difficulty with, and/or when it is known that the patient has difficulty with more than one process. The arrangement can include two strip-type electrode devices, shown as a first electrode device 717*a* and a second electrode device 717*b*. The first electrode device 717*a* can be positioned to extend over both the dorsal lateral prefrontal cortex 619 (e.g., the first selected region 617*a*), and the supplementary motor area 621 (e.g., the second selected region 617*b*). The second electrode device 717*b* can extend over the motor strip 620 (e.g., the third selected region 617*c*). In one aspect of this embodiment, each electrode device 717*a*, 717*b* can include a single row of contacts 732, and in other embodiments, each electrode device 717*a*, 717*b* can include multiple rows or other arrangements of contacts 732. In any of these embodiments, both electrode devices 717*a*, 717*b* can be coupled to one or more pulse generators and controllers (not shown in FIG. 7) to selectively provide electrical stimulation to target areas either simultaneously or sequentially, depending, for example, on whether the patient exhibits symptoms sequentially or simultaneously.

In other embodiments, the systems described above can be implanted and operated in still further manners. For example, one or more electrode devices can be implanted in a manner that places first and second electrical contacts proximate to different areas of the patient's brain. Electrical stimulation can then be applied simultaneously or sequentially to these areas to treat one or more neural dysfunctions, and the implantation site can be selected in a manner that does not necessarily require identifying the functional manifestation of the neural dysfunction. In a particular embodiment, the stimulation can be applied to any two (or more) of the motor cortex, the prefrontal cortex and the supplementary motor area. As used herein, the term motor cortex can include the primary motor cortex and/or the premotor cortex. The stimulation can be applied to one or both of the patient's brain hemispheres. In other embodiments, the stimulation can be applied to other multiple locations.

From the foregoing, it will be appreciated that specific embodiments of the invention have been described herein for purposes of illustration, but that various modifications may be made without deviating from the spirit and scope of the invention. For example, aspects of the invention described in the context of particular embodiments can be combined or eliminated in other embodiments. Many of the steps are described above in a particular order for purposes of illustration, but can be carried out in other orders as well. Further details of electrode system, techniques for visualizing target implant areas, and techniques for implanting electrodes are disclosed in the following corresponding U.S. applications, all of which are incorporated herein by reference: Ser. No. 10/731,731, filed. Dec. 9, 2003; Ser. No. 10/910,775, filed Aug. 2, 2004; Ser. No. 10/877,830, filed Jun. 25, 2004; and Ser. No. 10/731,852, filed Dec. 9, 2003. Accordingly, the invention is not limited except as by the appended claims.

We claim:

1. A method for reducing drug side effects on a patient, comprising:
   determining an aspect of the patient's functioning that is negatively affected by a drug in which the patient consumes as part of a therapy to treat a movement disorder or to treat symptoms associated with a movement disorder;
   positioning at least one electrode device having a plurality of electrical contacts such that at least one electrical contact is positioned below the patient's skull on the dura over a target cortical location selected from the group consisting of prefrontal cortex, supplemental motor cortex and motor cortex; and
   applying electrical stimulation to the cortical region of the patient's brain that is associated with the functioning such that the electrical stimulation reduces the drug side effects.

2. The method of claim 1 wherein determining an aspect of a patient's functioning includes determining an aspect of the patient's motor functioning that is influenced by the patient's consumption of drugs that are administered to reduce symptoms of Parkinson's disease.

3. The method of claim 1 wherein determining an aspect of a patient's functioning includes determining an aspect of the patient's cognitive functioning that is influenced by the patient's consumption of drugs that are administered for controlling symptoms of Parkinson's disease.

4. The method of claim 1 wherein determining an aspect of a patient's functioning includes determining an aspect of the patient's motor functioning that is influenced by the patient's consumption of drugs that are administered to reduce symptoms of a movement disorder.

5. The method of claim 1 wherein determining an aspect of a patient's functioning includes determining an aspect of the patient's cognitive functioning that is influenced by the patient's consumption of drugs that are administered to reduce symptoms of a movement disorder.

6. The method of claim 1 wherein the drug side effects comprises effects on the patient's cognitive and/or motor functioning.

7. The method of claim 6 wherein the effect on the patient's motor functioning comprises unwanted dyskinesias.

8. The method of claim 1 wherein the movement disorder is Parkinson's disease.

9. The method of claim 1 wherein the drug comprises a dopamine precursor or dopamine related compound.

10. A method for reducing the side effects of drug therapy in a Parkinson's patient comprising:
    identifying a patient in which the patient is receiving a drug therapy to reduce symptoms associated with Parkinson's disease;
    determining a motor function and/or cognitive complication associated with the patient's consumption of the drug therapy and based upon the complication positioning an electrode device having a plurality of electrical contacts such that at least one electrical contact is positioned below the patient's skull and on the dura over a target cortical location of the patient's brain associated with the complication selected from the group of cortical locations consisting of prefrontal cortex, supplemental motor cortex, and motor cortex;
    applying electrical signals to the plurality of electrical contacts to stimulate the target location of the patient's brain associated with the complication and thereby reducing the complication associated with the drug therapy.

* * * * *